United States Patent [19]

Egidio et al.

[11] Patent Number: 5,314,904
[45] Date of Patent: May 24, 1994

[54] PHARMACEUTICAL COMPOSITIONS CONTAINING RIFAXIMIN FOR TREATMENT OF VAGINAL INFECTIONS

[75] Inventors: Marchi Egidio, Casalecchio di Reno; Rotini L. Gabriele, Bologna, both of Italy; Desai Subhash, Grayslake; Grillli Massimo, Highland Park, both of Ill.

[73] Assignee: Alfa Wassermann S.p.A., Alanno, Italy

[21] Appl. No.: 899,421

[22] Filed: Jun. 16, 1992

[30] Foreign Application Priority Data

Dec. 17, 1991 [IT] Italy .................. 000476 A/91BO

[51] Int. Cl.$^5$ .......................... A61K 31/415
[52] U.S. Cl. .................. 514/394; 514/945; 514/967
[58] Field of Search .............. 514/394, 787, 788, 945, 514/967

[56] References Cited

PUBLICATIONS

CA 107(14):121087v, Cociasu et al., 1986.
The Merck Index, #8218, 11th Ed., 1989.
Remington's Pharmaceutical Sciences, 18th Ed., p. 1694–1712, 1990.

*Primary Examiner*—Frederick E. Waddell
*Assistant Examiner*—Kimberly R. Jordan
*Attorney, Agent, or Firm*—Bucknam and Archer

[57] ABSTRACT

Vaginal pharmaceutical compositions administrable through the topical route, particularly in the form of vaginal foams and creams containing a therapeutically effective amount of rifaximin (Common International Denomination) are useful in the treatment of vaginal infections, particularly bacterial vaginosis.

7 Claims, No Drawings

PHARMACEUTICAL COMPOSITIONS CONTAINING RIFAXIMIN FOR TREATMENT OF VAGINAL INFECTIONS

BACKGROUND OF THE INVENTION

The present invention relates to rifaximin (Common International Denomination) which is the compound 4-desoxy-4'-methyl-pyrido [1'2':1.2] imidazo [5.4-c] rifamycin SV, which is described in Italian Patent 1,154,655 and in U.S. Pat. No. 4,341,785. The substance has been described to be endowed with an antibacterial activity similar to the activity of rifampin [Venturini A. P. and Marchi E., Chemiotherapia, 5 (4), 257-256, (1986)]. However, its mechanism of action differs from rifampin in that it is not absorbed through the systemic route after oral administration [Venturini A. P., Chemotherapy, 29, 1-3, (1983) and Cellai L. et al., Chemiotherapia, 3, (6), 373-377, (1984)] due to the zwitterionic nature of the compound, which cannot be absorbed by the gastrointestinal tract [Marchi E. et al., J. Med. Chem., 28, 960-963, (1985)].

Due to this particular pharamcokinetic behavior, rifaximin has no toxicity at a dose of 2000 mg/kg/os, when administered orally in rats, and therefore, on the basis of the microbiological pharmacodynamic and toxicological data, this substance has been used as a drug for the therapy of bacterial gastroenteritis, neurological symptoms and clinical symptoms of hepatic encefalopathy and for the pre- and post-surgical treatment of the gastrointestinal tract [Alvisi V. et al., J. Int. Med. Res., 15, 49-56, (1987), Testa R. et al., Drugs Exptl. Clin. Res., 11, 387-392, (1985), Gruttadauria G. et al., Eur. Rev. Med. Pharm. Sci., 9, 100-105, (1987)].

The present invention relates to a novel therapeutic use of rifaximin in the treatment of vaginal infections, in particular bacterial vaginosis, because this antibiotic has now been shown to exhibit excellent activity in vitro (MIC) with respect to microorganisms such as *Bacteroides bivius-disiens, Gardnerella vaginalis, Mobiluncus* spp., *Neisseria gonorrhoeae, Lactobacillus* spp. and *Haemophilus ducreyi*, in addition, *Chlamydia trachomatis*, another organism, infecting the vaginal tract, has shown susceptibility to rifaximin.

The main cause of vaginal symptoms in women is due to bacterial vaginosis, which is characterized by an increase in the vaginal secretion of a white grayish color and which has a bad odor. This vaginal fluid shows the presence of bacterial flora which comprises mainly anaerobic bacteria such as *Gardnerella vaginalis* and the species *Bacteroides, Mobiluncus* and *Lactobacillus,* other aerobic bacteria such as *Haemophilus ducreyi* and *Neisseria gonorrhoeae* may also cause vaginal symptoms. Further the chemical composition shows an alteration in the presence of organic acids with increase of succinates and decrease of lactates in addition to the presence of some amines which have bad odor such as putrescine, cadaverine and trimethylamine.

Bacterial vaginosis generally shows scanty or no inflammation of the vaginal epithelium and resembles more of an alteration of the bacterial vaginal ecosystem than a real and proper infection of tissues or epithelium. This pathology is currently being treated mainly with metronidazole, clindamycin or ampicillin administered orally, but this method of use by the systemic route is frequently accompanied by serious side effects. In fact, metronidazole exhibits serious side effects particularly on the blood and on the central nervous system so much that in certain types of patients it has been necessary to discontinue the treatment and authorities in the medical field have recommended that women who use metronidazole should not breast feed (Martindale—The Extra Pharmacopoeia—29th Edition—1989—page 667).

Clindamycin also exhibits serious side effects, particularly on the gastrointestinal tract with serious forms of diarrhea and pseudo-membranous colitis that can even lead to the death of the patient (Martindale—The Extra Pharmacopoeia—29th Edition—1989—pages 198-199).

Rifaximin is not absorbed by the oral route [Venturini A. P., Chemotherapy, 29, 1-3, (1983)] nor by topical application [Venturini A. P. et al., Drugs Exptl. Clin. Res., 13, 4, 233-6, (1987)]. Compared with drugs currently used, rifaximin unquestionably exhibits a very substantial advantage, since there are no side effects.

DETAILED DESCRIPTION OF THE INVENTION

One objective of the present invention is to provide vaginal pharmaceutical compositions to be administered through the topical route, particularly vaginal foams and creams, containing a therapeutically effective amount of rifaximin, preferably between 50 mg and 500 mg, corresponding to the compound 4-desoxy-4'-methylpyrido[1'2':1.2]imidazo[5,4-c]rifamycin SV described in Italian Patent 1,154,655 and U.S. Pat. No. 4,341,785.

Another objective is to improve the method of treating a vaginal infection, particularly bacterial vaginosis, with compositions of the present application, and to provide a method for the preparation of the pharmaceutical compositions.

All pharmaceutical composition commonly used for the treatment of vaginal pathological conditions by the topical route may be advantageously used within the scope of the present invention. Vaginal foams, ointments, creams, gels, ovules, capsules, tablets and effervescent tablets may be effectively used as pharmaceutical compositions containing rifaximin which are capable of being administered by the topical route for the treatment of vaginal infections, including bacterial vaginosis.

The current invention relates to vaginal foam drug delivery system and cream as the preferred types of compositions and the clinical tests that have been carried out with these two types of preparations. The best clinical results have been achieved with the foam which, compared to the other pharmaceutical compositions, has unquestionable advantage of permitting rifaximin, which is not absorbed either by the systemic route nor by the topical route, the maximum possibility of contact with the vaginal mucosa, thus permitting the drug to achieve the best possible bactericidal action with respect to the pathologic agents. In fact, the system of distribution of the drug through the foam permits rifaximin to be distributed in an effective manner in the interior of the vagina, thus placing the drug in direct contact with the bacterial flora responsible for the bacterial infections.

The vaginal foam drug delivery system consists of a cylindrical canister made of aluminum, internally protected by a coating of epoxy-phenolic resins and provided with a valve and an applicator made of polyethylene. The formulation in the canister consists of suspension of micronized rifaximin having a particle size lower than 100 microns (<100μ) in mineral, vegetable or semi-synthetic oil in the presence of a thickening substance. The canister is closed with a valve through which a propellant gas is filled.

Many oily substances may be used in the present formulation. However, the main requirements for choice reside in their chemical stability and absence of toxicity with respect to the vaginal mucosa.

The preferred oily substances are USP mineral oil, liquid paraffin, vaseline oil, triglycerides of caprylic and capric acid, such as the substance known as Myritol ® 318 and polyoxyethylenated glycerides of oleic acid, such as Labrafil ® 2735 CS. The preferred thickening substances are cetostearyl alcohol, which is a mixture of cetyl alcohol and stearyl alcohol, hydrogenated castor oil and beeswax. Gaseous hydrocarbons, pure or as a mixture, chlorofluorocarbons, fluorocarbons, carbon dioxide, nitrogen, inert gases or their mixtures may be used as propellants. Dichlorodifluoromethane, propane, n-butane, isobutane or their mixtures, (55% of n-butane, 25% propane, 20% isobutane) known as Purifair ® 3.2, are the preferred propellants within the scope of the present invention or formulation.

The composition of the suspension maintaining the active component by weight, consists preferably of 2% to 8% of micronized ($<100\mu$) rifaximin, 2% to 6% of the thickening agent and 86% of the oil base. The proportion of the propellant gas is between 60% and 100% of the weight of the suspension.

The method of preparation of the formulation containing the vaginal foam drug delivery system involves several steps. In the first step, the thickening agent is melted in an aliquot of the oil base of 50% to 60%. This step is carried out in a melter by heating the mixture to 50° to 80° C. under stirring by agitation to obtain a practically homogeneous solution.

In the second step, a suspension of micronized rifaximin ($<100\mu$) is prepared in the remaining oil base by stirring at slow speed for 30 minutes under a light vacuum (500 mm Hg) in a turbo-diffuser, which is capable of operating under vacuum and is provided with a jacket for cooling and warming by water, equipped with an anchor-shaped stirring blade, a scraper and a whirling homogenizer.

The third step, the thickening agent (first step) is cooled to 40° to 50° C. and then added to the rifaximin preparation (step two) under slow stirring while simultaneously creating a light vacuum and cooling by means of cold water in the jacket until room temperature is reached.

The last step provides for the sub-division by means of a filling machine of the suspension prepared in the preceding step in individual canisters, which are then closed with a valve through which a propellant gas is introduced in an amount between 60% to 100% of the weight of the suspension.

Creams and gels, other base formulations that may be used in the vaginal administration of rifaximin, are prepared according to conventional methods for semi-solid compositions using excipients like vaseline, paraffin, vaseline oil, vegetable oils, animal oils, solid and liquid synthetic glycerides, waxes, liquid alkylpolysiloxanes, lanolin, lanolin alcohols, sorbitan esters, fatty alcohols, liquid/solid polyethylene glycols, propylene glycols, polyethylene, starch, derivatives of cellulose and carboxyvinylpolymers.

Ovules, capsules, tablets and effervescent tablets are other forms suitable for the vaginal administration of rifaximin. Ovules are similar to suppositories, ovoidal shaped and the excipients mainly used are semi-synthetic glycerides and polyethylene glycols and optionally also emulsifiers and surfactants.

The vaginal capsules are gelatinous envelopes within which is subdivided the suspension which is generally anhydrous and contains liquid paraffin, vaseline, dimethylpolysiloxanes, vegetable oils and semi-synthetic oils and thickening agents.

The tablets, shaped suitably for vaginal use, contain as main excipients lactose, starch, polyvinylpyrrolidone, cellulose derivatives, magnesium stearate, glycocol. The effervescent tablets contain chemical components (i.e. sodium bicarbonate with citric acid or tartaric acid), which are necessary to develop carbon dioxide in order to produce effervescence.

The efficacy of rifaximin in the treatment of vaginal infections has been demonstrated by the determination of its activity in vitro (minimum inhibitory concentration) to inhibit pathogenic bacterial flora that is present in vaginal fluid of the patients having these pathologies and particularly anaerobic bacteria such as *Gardnerella vaginalis, Bacteroides bivius-disiens* and the species *Mobiluncus* and *Lactobacillus* as well as aerobic bacteria such as *Neisseria gonorrhoeae* and *Haemophilus ducreyi*. The microbiologic activity has also been demonstrated against *Chlamydia trachomatis*.

The tests of anti-bacterial activity in vitro of rifaximin have been carried out on culture collections belonging to five hospitals, connected with three U.S. universities and two Canadian universities. Forty strains of *Bacteroides bivius-disiens*, 23 strains of *Gardnerella vaginalis*, 31 strains of the species *Lactobacillus* and 13 strains of *Mobiluncus*, 35 strains (from Iowa) and 25 strains (from Manitoba) of *Neisseria gonorrhoeae*, 25 strains of *Haemophilus ducreyi* and 6 strains of *Chlamydia trachomatis* have been analyzed. The determination of the minimum inhibitory concentration on the strains of the four types of anaerobic bacteria has been carried out according to NCCLS M11-T2 method (National Committee for Clinical Laboratory Standards. Methods for antimicrobial testing of anaerobic bacteria—second edition: Tentative Standard. NCCLS M11-T2, Villanova, Pa. NCCLS; 1989) on agar Wilken-Chalgren (Difco Laboratories, Detroit, Mich.) to which blood has been added.

The determination of the minimum inhibitory concentration with respect to *Neisseria gonorrhoeae* has been carried out according to the NCCLS M7-A2 method (National Committee for Clinical Laboratory Standards. Methods for dilution antimicrobial susceptibility tests for bacteria that grow aerobically—second edition; Approved Standard. NCCLS M7-A2. Villanova, Pa.:NCCLS; 1990).

The strains of *Neisseria gonorrhoeae* have been grown on chocolate agar for 24 hours at 35° C. in the presence of 5% carbon dioxide. After each material has been isolated, it is applied on a plate based on agar GC containing appropriate dilution of antibiotic and incubated in an atmosphere containing carbon dioxide for 25 hours at 35° C.

The strains of *Haemophilus ducreyi* have been grown on chocolate agar for 24 hours at 35° C. in an atmosphere of carbon dioxide. After each material has been isolated, it is applied on chocolate agar containing appropriate dilution of antibiotic (Hoban D. et al. "In vitro activity of lomefloxacin against *Chlamydia trachomatis, Neisseria gonorrhoeae, Haemophilus ducreyi, Mycoplasma hominis* and *Ureaplasma urealyticum*". Diagn.

Microbiol. Infect. Dis. 12, 83S–86S, 1989). The plates are incubated in an atmosphere containing carbon dioxide with increasing moisture at 35° C. for 48 hours.

Rifaximin has exhibited a significant in vitro activity with respect to the vaginal bacterial flora with a minimum inhibitory concentration value between 0.03 and 1 µg/mL with respect to the strains of the four types of anaerobic bacteria (*Gardnerella vaginalis, Bacteroides bivius-disiens, Mobiluncus* species and *Lactobacillus* species) and a value of 0.12 and >16 µg/ml with respect to *Neisseria gonorrhoeae, Chlamydia trachomatis* M.I.C. were >20 µg/mL; *Mycoplasma hominis* and *Ureaplasma urealyticum* were ≧64 µg/mL.

These values of minimum inhibitory concentration compare very favorably with the values obtained with the strains of the four types of anaerobic bacteria in the case of the three antibiotics presently used in the systemic route in the treatment of vaginal bacterial infections. In fact, metronidazole has shown values of minimum inhibitory concentrations between 1 and <16 µg/mL, ampicillin between 0.5 and >64 µg/mL, and clindamycin between 0.06 and 4 µg/mL. In order to finally demonstrate the real efficacy of the rifaximin compositions in the treatment of vaginal bacterial pathologies, clinical testing has been carried out in an Italian hospital with 35 patients affected by bacterial vaginosis using a vaginal foam, as described herein, and a cream.

Vaginal infections represent a common disease of female genital organs very frequently encountered in clinical practice. The incidence of bacterial vaginosis is in a constant increase due to several factors, such as oral and local contraceptives, increased use of antibiotics, greater sexual freedom.

On the basis of the in vitro antimicrobial activity, which has shown the optimum activity of rifaximin with respect to the common microorganisms responsible for the vaginal infections, a study has been carried out for the purpose of determining the clinical efficacy and microbiological efficacy of two compositions of rifaximin for vaginal use, the vaginal foam drug delivery system and the cream as described in examples 4 and 7 herein below.

The clinical and microbiological determination has been carried out with 35 women who were not pregnant, of age, and affected by bacterial vaginosis. In each case, the diagnosis was made on the basis of the following criteria: Presence of "clue cells" in an amount greater than 20% with respect to the cells of the vaginal epithelium, together with at least two of the following three symptoms: homogeneous vaginal secretion, pH of vaginal secretion greater than 4.7, fishy odor (amine) upon placing the vaginal secretion in contact with an aqueous solution of 10% potassium hydroxide.

The patients affected by vaginal protozoan, mycotic, viral and gonococcal infections have been excluded in this clinical test.

The control of clinical symptoms (pruritus, burning, leukorrhea, dysuria, edema and vulvo-vaginal erythema), cytological examination of the vaginal secretion and microbiological examination of the vaginal smear have shown that both pharmaceutical compositions that have been administered have effectively eliminated the clinical symptoms and have substantially reduced the percentage of "clue cells". Moreover, in a number of patients, pathogenic bacterial flora, such as *Gardnerella vaginalis, Mobiluncus* spp. *Bacteroides* spp. and *Streptococcus pyogenes* have been eliminated in the treatment with vaginal foam drug delivery system and the vaginal bacterial flora was normalized with the reappearance of the *Doderlein's bacillus.*

The vaginal foam drug delivery system exhibits therapeutic efficacy and patient acceptability compared to the cream. The success of the vaginal foam drug delivery system in eliminating the clinical symptoms 35 days after dosing is comprised between a minimum of 43.4% for vaginal erythema and 100% for dysuria, vulvar edema and erythema. The success of the cream is between a minimum of 60% for pruritus and a maximum of 86.7% for leukorrhea. Microbiological efficacy of the foam at 35 days after treatment showed the disappearance of all the pathogenic microorganisms in 86.6% of the patients, while the cream caused the disappearance of all pathogenic microorgamisms in 62.5% of the patients.

The vaginal foam drug delivery system was well accepted and tolerated by all patients. The cream formulation was also well tolerated although 1 patient treated with the cream withdrew from the study due to irritation. In addition, the patients have shown to be more pleased with the treatment with the vaginal foam because of the greater ease of manipulation and application and for the pleasant sensation of coolness, the so-called "cooling effect" which is typical of this type of formulation.

The results of the clinical investigation have demonstrated the efficacy of both pharmaceutical compositions containing rifaximin and in particular, of the vaginal foam drug delivery system in the treatment of vaginal infections and bacterial vaginosis. The results that have been obtained are similar to the results obtained with the conventional drugs used through the systemic route, such as metronidazole, clindamycin and ampicillin, but with the substantial advantage being obtained that the treatment is totally devoid of the disadvantageous side effects characteristic of the antibiotics mentioned above.

The examples reported herein below further illustrate the object of the present invention, but they should not be considered as a limitation to it.

EXAMPLE 1

Antibacterial activity of rifaximin on microorganisms present as pathogenic agents in vaginal infections The antibacterial activity in vitro (Minimum Inhibitory Concentration—MIC) of rifaximin has been evaluated with many strains of four active pathogenic agents present in vaginal infections and compared with three antibiotics (metronidazole, ampicillin, clindamycin) used in the systemic treatment of vaginal infections. Moreover, the MIC of rifaximin has been evaluated also with strains of *Chlamydia trachomatis, Mycoplasma hominis, Ureaplasma urealyticum, Neisseria gonorrhoeae* and *Haemophilus ducreyi.*

Forty strains of *Bacteroides bivius-disiens,* 23 strains of *Gardnerella vaginalis,* 31 strains of *Lactobacillus* spp., 13 strains of *Mobiluncus* spp., 6 strains of *Chlamydia trachomatis,* 60 strains of *Neisseria gonorrhoeae* and 25 strains of *Haemophilus ducreyi* were obtained by culture collections supplied from:

A. Department of Pathology, University of Iowa College of Medicine, Iowa City, Iowa
B. St. Francis Regional Medical Center, Wichita, Kans.
C. New England Deaconess Hospital, Boston, Mass.

D. University of Manitoba Health Science Center, Winnipeg, Manitoba
E. University of Alberta, Alberta, Canada.

The strains of anaerobic microorganisms have been subjected to the in vitro tests with rifaximin, metronidazole, ampicillin and clindamycin using the previously described method (National Committee for Clinical Laboratory Standards. Methods for antimicrobial testing of anaerobic bateria—second edition; Tentative Standard. NCCLS M11-T2, Villanova, Pa. NCCLS; 1989) using agar Wilken-Chalgren (Difco Laboratories, Detroit, Mich.) to which blood has been added.

The strains of the other microorganisms have been subjected to the in vitro tests with rifaximin. The determination of the MIC with respect to *Neisseria gonorrhoeae* has been carried out according to the NCCLS M7-A2 method, while the determination of th MIC with respect to *Chlamydia trachomatis, Mycoplasma hominis, Ureaplasma urealyticum* and *Haemophilus ducrey* has been carried out according to Hoban D. et al. "In vitro activity of lomefloxacin against *Chlamydia trachomatis, Neisseria gonorrhoeae, Haemophilus ducreyi, Mycoplasma hominis* and *Ureaplasma urealyticum.*" Diagn. Microbiol. Infect. Dis., 12, 83S–86S (1989).

The results of the tests of antimicrobial activity expressed as MIC in μg/mL are reported in Table I and demonstrate the positive behavior in vitro of rifaximin compared with the three systemic antibiotics commonly used.

the cells of the vaginal epithelium and the simultaneous presence of at least two of the following 3 factors:
A. Homogeneous vaginal secretion,
B. pH of the vaginal secretion greater than 4.7,
C. Fishy odor of the vaginal secretion.

Patients affected by vaginal infections of protozoan, fungal, viral and gonococcal origin were excluded. The patients were divided at random in two groups, one group being treated with the vaginal foam (Example 4) and the other group treated with cream (Example 7). The treatment consisted of one application prior to going to bed for five consecutive nights.

The microbiological, clinical and cytological controls were established at admission (Visit 1), 5 days after the end of the therapy (Visit 2) and 35 days after the end of the therapy (Visit 3). The last controls confirmed the results obtained in the Visit 2 controls.

The scoring measure is comprised between 0, absence of symptoms, and 3, serious symptoms, including subjective symptoms and those observed through objective examination. The results confirming the therapeutic activity of rifaximin in the treatment of bacterial vaginosis are reported in Table 2 for the vaginal foam and in Table 3 for the cream.

The therapeutic efficacy of both formulations in shown in Table 4 and shows a clear improvement for both compositions. The vaginal foam drug delivery system had a better (86.7%) cure rate compared to the cream formulation (56.2%).

TABLE 1

| Microorganism | Number of Strains | Antimicrobial Agents | MIC (μg/mL) 50% | MIC (μg/mL) 90% | Range of Concentration Value |
|---|---|---|---|---|---|
| *Bacteroides bivius-disiens* | 40 | Rifaximin | 0.12 | 0.25 | ≦0.03–0.5 |
| | | Ampicillin | 4 | 64 | ≦0.5–>64 |
| | | Clindamycin | ≦0.06 | <0.06 | ≦0.06 |
| | | Metronidazole | 2 | 4 | 0.5–8.0 |
| *Gardnerella vaginalis* | 23 | Rifaximin | 0.5 | 1 | 0.25–1.0 |
| | | Ampicillin | ≦0.5 | <0.5 | ≦0.5–2 |
| | | Clindamycin | ≦0.06 | <0.06 | ≦0.06–0.25 |
| | | Metronidazole | >16 | >16 | 4–>16 |
| *Lactobacillus* spp. | 31 | Rifaximin | 0.12 | 0.5 | ≦0.3–1 |
| | | Ampicillin | ≦0.5 | 1 | ≦0.5–2 |
| | | Clindamycin | 0.25 | 4 | ≦0.06–4 |
| | | Metronidazole | >16 | >16 | >16 |
| *Mobiluncus* spp. | 13 | Rifaximin | ≦0.03 | <0.03 | ≦0.03 |
| | | Ampicillin | ≦0.5 | 4 | ≦0.5–4 |
| | | Clindamycin | ≦0.06 | <0.06 | ≦0.06 |
| | | Metronidazole | >16 | >16 | 1–>16 |
| *Chlamydia trachomatis* | 6 | Rifaximin | — | <20 | <10–20 |
| *Mycoplasma hominis* | 20 | Rifaximin | 64 | ≧64 | ≧64 |
| *Ureaplasma urealyticum* | 25 | Rifaximin | 64 | >64 | 32–>64 |
| *Neisseria gonorrhoeae* | 60 | Rifaximin | 0.25 | 16 | 0.12–>16 |
| *Haemophilus ducreyi* | 25 | Rifaximin | 0.25 | 0.5 | 0.03–0.5 |

EXAMPLE 2

Clinical evaluation of a vaginal foam and a cream containing rifaximin

The clinical evaluation has been carried out in San Martino Hospital in Geneva with 30 women, not pregnant, affected by bacterial vaginosis. The diagnosis of bacterial vaginosis was made on the basis of the presence of "clue cells" in an amount greater than 20% of Table 5 reports the results of microbiological tests carried out with bacterial cultures present in the vaginal smears removed from the patient prior to the beginning of the treatment (Visit 1) and after the treatment (Visits 2 and 3). Prior to the beginning of treatment, the pathogenic bacterial flora was constituted essentially by *Gardnerella vaginalis, Mobiluncus* spp. and with less frequency by *Streptococcus pyogenes* and *Bacteroides* spp.

TABLE 2

Clinical results with women affected by bacterial vaginosis treated with vaginal foam prepared according to example 4.

| SIGNS & SYMPTOMS | VISIT 1 | VISIT 2 | % CHANGE BETWEEN VISITS 1 & 2 | VISIT 3 | % CHANGE BETWEEN VISITS 1 & 3 |
|---|---|---|---|---|---|
| Pruritus | 1.15 | 1.00 | 13.0 | 0.54 | 53.0 |
| Burning | 1.77 | 0.61 | 65.5 | 0.08 | 95.5 |
| Leukorrhea | 2.46 | 1.08 | 56.1 | 0.85 | 65.4 |
| Dysuria | 1.15 | 0.00 | 100.0 | 0.00 | 100.0 |
| Vulvar Edema | 0.92 | 0.31 | 66.3 | 0.00 | 100.0 |
| Vulvar Erythema | 1.08 | 0.08 | 92.6 | 0.00 | 100.0 |
| Vaginal Edema | 0.69 | 0.08 | 88.4 | 0.08 | 88.4 |
| Vaginal Erythema | 1.00 | 0.91 | 71.3 | 0.61 | 43.4 |

TABLE 3

Clinical results with women affected by bacterial vaginosis treated with cream prepared according to example 7.

| SIGNS & SYMPTOMS | VISIT 1 | VISIT 2 | % CHANGE BETWEEN VISITS 1 & 2 | VISIT 3 | % CHANGE BETWEEN VISITS 1 & 3 |
|---|---|---|---|---|---|
| Pruritus | 1.50 | 0.90 | 40.0 | 0.60 | 60.0 |
| Burning | 1.60 | 0.80 | 50.0 | 0.40 | 75.0 |
| Leukorrhea | 2.50 | 0.11 | 95.6 | 0.11 | 95.6 |
| Dysuria | 1.10 | 0.10 | 90.00 | 0.10 | 90.9 |
| Vulvar Edema | 1.20 | 0.40 | 66.7 | 0.20 | 83.3 |
| Vulvar Erythema | 1.00 | 0.20 | 80.0 | 0.20 | 80.0 |
| Vaginal Edema | 1.20 | 0.30 | 75.0 | 0.10 | 91.7 |
| Vaginal Erythema | 1.50 | 0.60 | 60.0 | 0.30 | 80.0 |

TABLE 4

Results of cytological examination carried out with women affected by bacterial vaginosis.

| PATIENT STATUS | NUMBER OF PATIENTS FOAM | NUMBER OF PATIENTS CREAM |
|---|---|---|
| Enrolled | 17 | 18 |
| Curred at Visit 2 | 13 | 9 |
| Curred at Visit 3 | 13 | 9 |
| % Curred at Visit 3 | 86.7% | 56.2% |
| Treatment Failure | 2 | 6 |
| Dropped Due to Irritation | 0 | 1 |
| Lost to Follow-Up | 2 | 2 |

TABLE 5

Culture results of patients treated with foam drug delivery system and cream.

| PATHOGENS ISOLATED | VISIT 1 FOAM n = 17 | VISIT 1 CREAM n = 18 | VISIT 2 FOAM n = 15 | VISIT 2 CREAM n = 16 | VISIT 3 FOAM n = 13 | VISIT 3 CREAM n = 10 |
|---|---|---|---|---|---|---|
| Gardnerella | 14 | 15 | 1 | 5 | 0 | 0 |
| Gardnerella & Mobiluncus | 3 | 2 | 0 | 0 | 0 | 0 |
| Gardnerella & Streptococcus | 0 | 0 | 1 | 1 | 0 | 0 |
| Streptococcus | 0 | 0 | 1 | 1 | 0 | 0 |
| Enterobacter | 0 | na | 1 | na | 0 | na |
| Gardnerella & Candida | 0 | 0 | 0 | 1 | 1 | 1 |

EXAMPLE 3

System of distribution of foam containing rifaximin to be administered vaginally

| Composition of Each Canister | |
|---|---|
| - Rifaximin | 200 mg |
| - Cetyl stearyl alcohol USP | 160 mg |
| - Mineral oil USP | 3640 mg |
| - Mixture of n-butane/propane/isobutane 55:25:20 (Purifair ® 3.2) | 3150 mg |

In a stainless steel container provided with an external jacket for warming and with a stirring blade, melt 3.2 kg cetyl stearyl alcohol USP in 43.8 kg mineral oil USP to a temperature of +65°±5° C. under stirring up to complete solution. In a turbo vacuum diffuser made of stainless steel provided with a jacket for heating and cooling with water and also provided with a stirring blade, scraper and central turbo homogenizer, introduce 29 kg mineral oil USP and 4 kg micronized (<100μ) rifaximin. The material is kept under stirring at a low rate for 30 minutes under a light vacuum (500 mm of mercury). A solution of cetyl stearyl alcohol in mineral oil USP, previously cooled to 45° C., is added to this suspension with continuous stirring under light vacuum for an additional 10 minutes while simultaneously cooling the mixture to room temperature. The mixture is subdivided by means of a filling machine in 20,000 canisters, which are then closed with a polyethylene valve and filled with propellant gas Purifair ® 3.2 and finally a delivery means provided with a polyethylene tube is inserted in the valve.

EXAMPLE 4

Pharmaceutical composition of foam containing rifaximin to be administered vaginally

| Composition of each canister | |
|---|---|
| - Rifaximin | 200 mg |
| - Cetyl stearylic alcohol USP | 160 mg |
| - Liquid paraffin | 3640 mg |
| - Dichlorofluoromethane | 3000 mg |

The canisters are made in a manner similar to example 3.

EXAMPLE 5

Pharmaceutical composition of foam containing rifaximin to be administered vaginally

| Composition of each canister | |
|---|---|
| - Rifaximin | 200 mg |
| - Cetyl stearylic alcohol USP | 160 mg |
| - Triglycerides of caprylic & capric acid (Myritol ® 318) | 3640 mg |
| - Mixture n-butane/propane/isobutane 5:25:20 (Purifair ® 3.2) | 3300 mg |

The canisters are made in a manner similar to Example 3.

EXAMPLE 6

Pharmaceutical composition of foam containing rifaximin to be administered vaginally

| Composition of each canister | |
|---|---|
| - Rifaximin | 100 mg |
| - Cetyl stearylic alcohol USP | 160 mg |
| - Polyoxyethylenated glycerides of oleic acid (labrafil ® 2735 CS) | 3740 mg |
| - Mixture n-butane/propane/isobutane 55:25:20 (Purifair ® 3.2) | 3200 mg |

The canisters are produced in the same manner as described in Example 3.

EXAMPLE 7

Pharmaceutical composition of cream containing rifaximin

| Percent of composition of the cream | |
|---|---|
| - Rifaximin | 5% |
| - White vaseline | 10% |
| - Liquid paraffin | 72% |
| - White wax | 3% |
| - Hydrogenated caster oil | 5% |
| - Methyl glucose dioleate | 5% |

In a turbo diffuser similar to the apparatus used in Example 3, a mixture consisting of white vaseline, liquid paraffin, white wax and methyl glucose dioleate is melted by warming to a temperature of 72° C. under slow stirring. Hydrogenated castor oil is added to the mixture, which is then homogenized with a central turbo homogenizer. After cooling to room temperature, micronized rifaximin ($<100\mu$) is added to the mixture and then homogenized with the turbo diffuser under a light vacuum of 500 mm of mercury. The resulting cream is filled into suitable containers.

EXAMPLE 8

Pharmaceutical composition of vaginal ovules containing rifaximin

| Composition of each ovule | |
|---|---|
| - Rifaximin | 200 mg |
| - Solid semi-synthetic glycerides | 1600 mg |

In a stainless steel container equipped with exterior jacket for warming and cooling, the solid semi-synthetic glycerides is placed, along with the micronized ($<100\mu$) rifaximin. The mixture is homogenized with the Ultra Turax homogenizer and then divided into individual containers of the shape suitable for vaginal use.

EXAMPLE 9

Pharmaceutical composition of vaginal capsules containing rifaximin

| Composition of each vaginal capsule | |
|---|---|
| - Rifaximin | 150 mg |
| - Liquid glycerides | 900 mg |
| - Silica | 5 mg |

A suspension of micronized ($<100\mu$) rifaximin and silica is homogenized in a stainless steel container containing the liquid glycerides by means of the homogenizer Ultra Turax. The suspension is then poured into gelatin capsules for vaginal use.

EXAMPLE 10

Pharmaceutical composition of vaginal tablets containing rifaximin

| Composition of each vaginal capsule | |
|---|---|
| - Rifaximin | 200 mg |
| - Lactose | 1200 mg |
| - Corn starch | 200 mg |
| - Polyvinylpyrrolidone | 50 mg |
| - Magnesium stearate | 12 mg |
| - Talcum | 7 mg |

Micronized ($<100\mu$) rifaximin is granulated with lactose, corn starch and a solution of polyvinylpyrrolidone in ethyl alcohol. The granulates are dried in a dryer and screened on a 1 mm screen. To the granulate add talcum and magnesium stearate and the mixture is compressed to obtain tablets of the shape suitable for vaginal use.

EXAMPLE 11

Pharmaceutical composition of effervescent vaginal tablets containing rifaximin

| Composition of each vaginal effervescent capsule | |
|---|---|
| - Rifaximin | 100 mg |
| - Citric acid | 260 mg |
| - Sodium bicarbonate | 300 mg |
| - Magnesium stearate | 10 mg |
| - Talcum | 8 mg |
| - Polyvinylpyrrolidone:ethyl alcohol | 35 mg |

Polyvinylpyrrolidone is dissolved in ethyl alcohol. A mixture of citric acid and one-half of the micronized ($<100\mu$) rifaximin is granulated with one-half of the polyvinylpyrrolidone:alcohol solution. The other one-half of the polyvinylpyrrolidone:alcohol solution is used to granulate the mixture formed by the sodium bicarbonate and the remaining half of rifaximin. The two granulates are dried separately, screened on a 1 mm screen, and then mixed together with talcum and magnesium stearate. The resulting mixture is compressed to obtain tablets of the shape suitable for vaginal use.

What is claimed is:

1. A method of treatment of a vaginal infection which consists of administering topically to a subject in need of treatment a vaginal pharmaceutical composition containing a therapeutically effective amount of Rifaximin in the form of a foam, a cream, a gel, a vaginal ovule or a vaginal capsule.

2. The method according to claim 1 wherein said treatment is with said foam, the flora of *Gardnerella vaginalis, Mobiluncus* spp., *Bacteroides* spp. and *Streptococcus pyogenes* are eliminated and the vaginal bacterial flora is normalized with the reappearance of the *Doderlein's bacillus*.

3. The method according to claim 1 wherein said vaginal infection consists of bacterial vaginosis.

4. The method of treatment of a vaginal infection according to claim 1 which consists of applying by the topical route a pharmaceutically effective amount of Rifaximin to a patient in need of said treatment.

5. The method according to claim 4 wherein said vaginal infection consists of bacterial vaginosis.

6. The method according to claim 4 wherein said topical application is carried out by means of a vaginal foam.

7. The method according to claim 4 wherein said topical application is carried out by means of a cream.

* * * * *